United States Patent [19]

Sanderson et al.

[11] Patent Number: 5,072,060
[45] Date of Patent: Dec. 10, 1991

[54] PROCESS FOR THE PRODUCTION OF PRIMARY BRANCHED ALCOHOLS

[75] Inventors: John R. Sanderson, Leander; Edward T. Marquis, Austin, both of Tex.

[73] Assignee: Texaco Chemical Company, White Plains, N.Y.

[21] Appl. No.: 590,733

[22] Filed: Oct. 1, 1990

[51] Int. Cl.$^5$ ..................... C07C 29/38; C07C 71/125
[52] U.S. Cl. .................................................... 568/878
[58] Field of Search ........................................ 568/878

[56] References Cited

U.S. PATENT DOCUMENTS 2,818,440 12/1957 Rust et al. ........................... 568/821

FOREIGN PATENT DOCUMENTS 793428 4/1958 United Kingdom ................. 568/878

OTHER PUBLICATIONS

Rust et al., "J. Am. Chem. Soc." vol. 80 (1958) pp. 6148–6149.

Primary Examiner—J. E. Evans
Attorney, Agent, or Firm—Jack H. Park; Kenneth R. Priem; David L. Mossman

[57] ABSTRACT

A method for the preparation of branched primary alcohols comprises reacting a normal alkane with formaldehyde in non-aqueous media in the presence of a free radical initiator. The reaction involves the preferential addition of formaldeyhde to internal carbon atoms of the normal alkane, resulting in a branched primary alcohol containing one carbon more than the alkane reactant. The product alcohols are obtained as mixtures of positional isomers.

19 Claims, No Drawings

PROCESS FOR THE PRODUCTION OF PRIMARY BRANCHED ALCOHOLS

BACKGROUND OF THE INVENTION

1. Technical Field of the Invention

This invention relates to the manufacture of alcohols. More particularly, this invention relates to a method for the preparation of primary branched alcohols from certain normal hydrocarbons and formaldehyde in the presence of free radical initiators. The product alcohols are obtained as a mixture of species which can have one more carbon atom than the starting material. These alcohols may be used as intermediates for the production of detergents and plasticizers and as solvents.

2. Information Disclosure Statement

Among the many alcohols of commercial significance, fatty alcohols and their derivatives are of great importance as surfactants, plasticizers and as intermediates for the production of monomers, polymers, lubricating oils and the like. The most widely used are the fatty alcohols having from 12 to 15 carbon atoms. The "detergent" alcohols are defined by the *Chemical Economics Handbook*, Alcohols, 609.5021G (SRI Intl.1987) as alcohols having twelve or more carbon atoms and having a carbon backbone with a "high degree of linearity". This is a convenient category for such alcohols, since they are used primarily in detergent applications (although also used in a number of diverse applications) and alcohols having less than twelve carbons are used to a greater extent in other products and are often referred to as "plasticizer" alcohols. Highly branched alcohols having more than twelve carbons are also excluded. Alcohols derived from animal fats and vegetable oils have carbon backbones that are completely linear, but those derived from ethylene and n-paraffins may range from 35 to 99 percent linear. However, the types and levels of branching still permit the use of such alcohols in most detergent applications. Plasticizer alcohols, i.e. the primary aliphatic alcohols having from 4 to 13 carbons (excluding the linear versions with 12 or 13 carbons) are discussed in the *Chemical Economics Handbook*, Id. at 609.4021C.

There are many methods known in the art for the preparation of alcohols. See Buehler and Pearson, *Survey of Organic Synthesis* Wiley Interscience, New York, 174, (1970). For example, solvolysis of esters, halides, xanthates, amines, cyclic ethers etc. produce a variety of alcohols. These alcohols always contain the same number of carbon atoms as the starting material. This can be represented by the following equation:

Paraffinic hydrocarbons such as n-dodecane can be converted to corresponding straight-chain alcohols by direct oxidation, as described by I]am et al. in "Liquid-Phase Oxidation of n-Dodecane in the Presence of Boron Compounds", *Ind. Eng. Chem. Prod. Res. Dev.*", Vol. 20, pp. 315–19 (1981).

It is known to prepare alcohols which contain one carbon more than the starting material by hydroformylation (the oxo process) of olefins. This process is not new in the art and can be represented as follows:

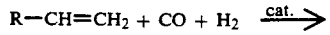

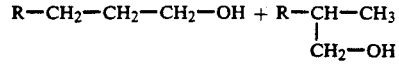

Formaldehyde may be added to olefins to form alcohols with one more carbon than the starting olefin (Arundale and Mikeska, Chem. Rev., Vol. 51, pp. 505, 506 and 528-39, (1952).

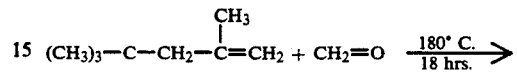

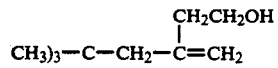

Oyama discloses the reaction of primary and secondary alcohols with formaldehyde in the presence of free radical generators to produce glycols in *J. Org. Chem.*, Vol. 30, pp. 2429-32 (1965). Kollar in U.S. Pat. No. 4,337,371 disclosed a method for the preparation of ethylene glycol wherein methanol and formaldehyde are reacted in the presence of an organic peroxide and water to form ethylene glycol. Yeakey and Applicant Sanderson disclose in coassigned U.S. Pat. No. 4,550,184 a method for the preparation of 2-hydroxymethyl-1,3-dioxolane from 1,3-dioxolane and formaldehyde in the presence of an organic peroxide. See also coassigned U.S. Pat. No. 4,628,108, in which an ionizable metal salt is used in conjunction with the organic peroxide. An article by Sanderson et al., "Free Radicals in Organic Synthesis. A Novel Synthesis of Ethylene Glycol Based on Formaldehyde," *J. Org. Chem.*, Vol. 52, pp. 3243-46 (1987), discloses the reaction of 1,3-dioxolane with formaldehyde in the presence of free radical initiators to form an intermediate which can be catalytically hydrogenated to ethylene glycol.

U.S. Pat. No. 2,818,440 discloses processes for additions of methylol groups to saturated hydrocarbons, including linear paraffins and cycloparaffins, which employ formaldehyde and organic peroxides. The methylol group can be added to an internal carbon of a linear paraffin. In the preferred mode, a saturated organic compound such as a paraffin or cycloparaffin is in a liquid phase in which the peroxide is dissolved, while the formaldehyde is present in a separate, generally aqueous, liquid phase. Alternatively, gaseous formaldehyde can be added to such a liquid organic phase in the reactor. See Rust et al., "Free Radical Addition of Cyclopentane and Cyclohexane to Formaldehyde", *J. American Chem. Soc.* Vol. 80, pp. 6148-49 (1958).

Despite the various routes described and the ones which have been devised, there is still a need for a method for producing primary branched alcohols from readily available but non-reactive normal hydrocarbons such as n-alkanes.

Additionally, it would be an advance in the art to prepare branched alcohols from normal hydrocarbons.

SUMMARY OF THE INVENTION

An object of the present invention is an improved process for the production of primary branched alcohols from normal alkanes, especially for the production of branched alcohols in the detergent range of carbon numbers. Other objects and advantages of the invention will be apparent from the following detailed description, including the appended claims.

It has been surprisingly discovered in accordance with the present invention that when certain normal saturated hydrocarbons are reacted with formaldehyde in the presence of a free radical initiator the reaction preferentially involves the addition of the formaldehyde to an intermediate carbon of the hydrocarbon to form primary branched alcohols. The formaldehyde is preferably introduced in the form of paraformaldehyde or trioxane, and the reaction is preferably carried out in non-aqueous or anhydrous media. These conditions are believed to increase the yield of the desired primary branched alcohols relative to byproducts such as n-alkanols and diols. The products obtained are mixtures of such primary branched alcohols having a methylol group bonded to one of various internal carbon positions in the alkane substrate. The reaction products formed contain significant quantities of primary branched alcohols which contain one more carbon than the starting material. The relationship between the reactants and products can be expressed by the equatron below:

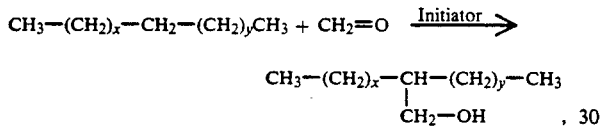

where x and y can be 0, 1, 2, 3, ... up to about 15 and x + y = from 0 to 15, preferably 6 to 14. Thus, the normal alkane starting materials can have from about 3 to about 18 carbon atoms, while the corresponding product alcohols will have from about 4 to about 19 carbon atoms. Mixtures of suitable alkanes such as commercially available fractions of petroleum oils can be employed as reactants, resulting in product mixtures varying in molecular weight as well as methylol group position. Although products based upon substantially linear alkanes are preferred, the invention can be practiced with starting materials which are lightly branched, i.e., containing no more than two methyl or ethyl side chains per molecule.

DETAILED DESCRIPTION OF THE INVENTION

Starting Materials

The starting materials for the instant invention are certain normal hydrocarbons, formaldehyde and a free radical initiator.

In the instant invention where normal alkanes are reacted with formaldehyde in the presence of a free radical initiator to produce primary branched alcohols the reaction can be represented by the equation above. The product branched primary alcohols are obtained as mixtures of positional isomers.

The starting materials for the present invention comprise normal hydrocarbons, having from 3 to about 18 carbon atoms, preferably normal alkanes having from about 8 to about 18 carbon atoms. The normal alkanes which can be used in the process of the invention most preferably include those containing about 10 to 14 carbons, which include n-decane, n-undecane, n-dodecane, n-tridecane and n-tetradecane. These materials produce alcohol products in the detergent range. Mixtures of alkanes can be employed. The detergent range alcohols (having about 6 to about 14 carbon atoms) can be reacted with ethylene oxide to produce nonionic detergents; see e.g. Kirk-Othmer's *Encyclopedia of Chemical Technology*, Third Edition, Vol. 22, page 360 (New York 1980). The light r alcohols can be employed as additives or blending ag₁. 's for motor fuels and as intermediates for the production of ethers which are also useful as additives and blending agents for fuels.

Formaldehyde may be employed in its conventional monomeric form as an aqueous formalin solution (37 percent formaldehyde), in "inhibited" methanol solution, as gaseous formaldehyde, as paraformaldehyde, or as trioxane. Paraformaldehyde or trioxane are the preferred starting materials. Gaseous formaldehyde can also be employed.

The free-radical initiator employed in the process of the present invention is preferably selected from the organic peroxides, organic hydroperoxides or certain azo compounds.

Suitable organic peroxides have the following formulas:

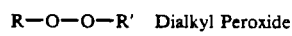

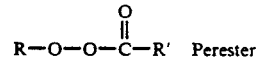

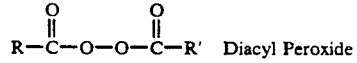

In the organic peroxide R and R' are each an alkyl or aralkyl group having 1 to 20 carbon atoms. Organic peroxides which may be used include di-tert-butyl peroxide, methyl-tert-butyl peroxide, di-cumyl peroxide, tert-butyl cumyl peroxide, tert-butyl perbenzoate etc. The preferred organic peroxide is di-tert-butyl peroxide.

Hydroperoxides which are substantially oil-soluble, such as tert-butyl hydroperoxide, tert-amyl hydroperoxide and triphenylmethyl hydroperoxide, can be used, but product yields would be expected to be lower.

Suitable azo compounds can have structures represented by the following formula:

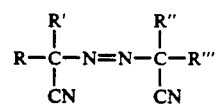

wherein R, R', R", R'" may be alike or different and may be alkyl as well as aralkyl. R, R', R", R'" can contain from 1 to 12 carbon atoms. Representative compounds include 2,2'-azobis(2-methylpropionitrile).

Reaction Conditions

In the reactions of the present invention the desired product of the invention is an equimolar addition product of the normal alkane hydrocarbon and formaldehyde. A molar excess of either reactant may be used, but it is preferred to use the normal alkane in excess, since it also serves as the solvent for the reaction and the product yield has been found to vary with the ratio of alkane to formaldehyde. While the ratios of the reactants are conveniently expressed in terms of moles per mole or in terms of weight (as in the examples herein), the number of available methylene groups in the hydrocarbon per mole of formaldehyde must be considered in selecting ratios from the above ranges. In addition, the selection of molar ratios which provide a high ratio of such available methylene groups to formaldehyde tends to favor high yields of the desired products in which a single methylol group is added to a methylene group. Generally the molar ratio of alkane to formaldehyde should be in the range of from about 0.3 to about 5, preferably from about 0.7 to about 4, most preferably from about 1 to about 3, or say about 2:1. Within these preferred ranges, adjustments should be made for different reaction temperatures and proportions of the initiator to the alkane.

The organic peroxide, hydroperoxide or azo compound is suitably used in an amount ranging from about 0.2 to 25 wt percent based o the branched hydrocarbon. Preferably, from about 2 to 15 wt percent of the organic peroxide is used.

If organic peroxides or hydroperoxides are used as the free radical initiator, the reaction is suitably conducted at a temperature within the range of about 80° C. to 280° C. and more preferably within the range of about 80° C. to about 180° C. With azo compounds, the temperature should be within the range of from about 40° C. to about 120° C.

The reaction can be conducted at any suitable pressure of atmospheric or above, but is preferably conducted at superatmospheric pressure. The preferred pressure is between atmospheric and about 100 psi.

In all embodiments, reaction times of from about 0.10 to about 10 hours may be employed with satisfactory results. Preferably, the reaction time will be in the range of about 1 to about 5 hours.

In all embodiments the reaction may be conducted in inert solvents such as chlorobenzene, bromobenzene, nitrobenzene, benzene, acetonitrile, tert-butyl alcohol, etc. but there is no advantage in doing so. The normal alkane starting material is a satisfactory solvent and reaction medium. The reaction can be carried out in the liquid state, in the gaseous state or in mixed states wherein the reactants are at least partially in the vapor state. Paraformaldehyde and trioxane are generally introduced as solids, but produce formaldehyde in solution or gaseous form at elevated temperatures.

At the end of the reaction, the reaction mixture may be separated into components to recover the product by any suitable technique such as distillation, filtration, solvent extraction, etc.

As indicated earlier, the alcohol products of this invention may be useful as intermediates for the production of detergents, plasticizers, monomers and polymers, lubricating oils and the like, and directly as solvents and fuel additives. A preferred application is the production of nonionic detergents.

EXAMPLES

The present invention is further illustrated by the following non-limiting examples.

EXAMPLE 1

First Reduction to Practice n-Dodecane (99 percent +, 50.0 g), paraformaldehyde (10.0 g), and di-tert-butyl peroxide (5.0 g) were charged to a 300 cc stainless steel autoclave equipped with a glass liner and magnedrive stirrer. The autoclave was sealed and the mixture heated slowly (ca. 1 hr.) to 150° C. and held at 150° C. for four hours. The mixture was then cooled to ambient temperature, vented and decanted from a small amount of solid. The liquid products were analyzed by GC. The products included 2.48 weight percent tridecanols (primary branched alcohols) and a small viscous lower layer which was rich in tert-butyl alcohol, acetone and tridecanols.

EXAMPLE 2 n-Dodecane (99 percent +, 80 ml), paraformaldehyde (5.0 g), and tert-butyl peroxybenzoate were charged to a 200 ml round-bottomed flask, equipped with water-cooled condenser, heating mantle, and magnetic stirrer. The mixture was heated for 4.0 hours at 135° C. GC analysis indicated the presence of 1.36 wt. percent tridecanols.

EXAMPLE 3 n-DodeCane (100.0 g), paraformaldehyde (10.0 g), and di-tert butyl peroxide (6.0 g) were charged to a 500 cc stainless-steel "zipper" autoclave. This mixture was heated at 150° C. for 6.0 hours. The reaction mixture was then cooled to ambient temperature, vented, and a liquid product (112.7 g) obtained. A lower viscous phase (15 g) was also obtained. Analysis of the upper layer by GC/FTIR indicated the presence of 3.52 area percent tridecanols and 0.87 area percent tridecanol formate ester. Analysis of the lower layer indicated the presence of 13.5 area percent tridecanols.

EXAMPLE 4 n-Dodecane (100.0 g), paraformaldehyde (12.0 g), di-tert-butyl peroxide (10.0 g) and tert-butyl alcohol (25.0 g) were charged to a 500 cc stainless-steel "zipper" autoclave equipped with stirrer, heating means, etc. The mixture was heated at 150° C. for 5.0 hours. The reaction mixture was then cooled to ambient temperature, vented and 130.0 g of homogeneous solution obtained. Analysis of the reactor effluent by GC/FTIR indicated the presence of 2.55 area percent tridecanols. There was only 0.08 area percent tridecanol formate present.

EXAMPLE 5 n-Decane (100.0 g), paraformaldehyde (17.0 g) and di-tert-butyl peroxide (13.0 g) were charged to a 500 cc stainless-steel "zipper" autoclave equipped with stirrer, heating mantle, etc. The reaction mixture was then heated to 150° C. and held at 150° C. for 6.0 hours. The mixture was then cooled to ambient temperature, vented and 126.4 g liquid obtained. Analysis by GC/FTIR indicated the presence of 3.2 area percent undecanols. There was 0.4 area percent undecanol formates also present.

EXAMPLE 6 n-Dodecane was reacted with paraformaldehyde in the presence of di-tert-butyl peroxide (DTBP) under the conditions indicated in Table 1.

A variable study was conducted and the reaction mixtures analyzed using GC. analysis. Representative results are shown in Table 1.

TABLE 1

Reaction of n-Dodecane with Formaldehyde Under Various Conditions

| Example No. | Alkane[1]/ Formaldehyde | M/R[4] | Alkane[1]/ DTBP | Time (HR) | Temp. (°C.) | Product (wt %) |
|---|---|---|---|---|---|---|
| 6[2] | 20.0 | 3.5 | 20.0 | 4.0 | 150.0 | 3.14 |
| 7[2] | 10.0 | 1.8 | 20.0 | 4.0 | 150.0 | 3.58 |
| 8[2] | 5.0 | 0.9 | 20.0 | 4.0 | 150.0 | 4.19 |
| 9[3] | 20.0 | 3.5 | 10.0 | 4.0 | 150.0 | 8.08 |

TABLE 1-continued

Reaction of n-Dodecane with Formaldehyde Under Various Conditions

| Example No. | Alkane[1]/ Formaldehyde | M/R[4] | Alkane[1]/ DTBP | Time (HR) | Temp. (°C.) | Product (wt %) |
|---|---|---|---|---|---|---|
| 10[3] | 20.0 | 3.5 | 10.0 | 4.0 | 150.0 | 7.19 |
| 11[3] | 10.0 | 1.8 | 10.0 | 4.0 | 150.0 | 7.45 |
| 12[3] | 10.0 | 1.8 | 10.0 | 4.0 | 150.0 | 5.51 |
| 13[3] | 5.0 | 0.9 | 10.0 | 4.0 | 150.0 | 5.11 |
| 14[3] | 5.0 | 0.9 | 10.0 | 4.0 | 150.0 | 2.72 |
| 15[3] | 10.0 | 1.8 | 6.67 | 4.0 | 150.0 | 8.49 |
| 16[3] | 10.0 | 1.8 | 6.67 | 4.0 | 150.0 | 6.81 |
| 17[3] | 10.0 | 1.8 | 6.67 | 6.0 | 140.0 | 5.9 |
| 18[3] | 5.0 | 0.9 | 10.0 | 6.0 | 140.0 | 3.60 |
| 19[3] | 6.67 | 1.33 | 6.67 | 4.0 | 150.0 | 6.51 |
| 20[3] | 20.0 | 3.5 | 6.67 | 4.0 | 150.0 | 7.38 |
| 21[3] | 5.0 | 0.9 | 25.0 | 4.0 | 150.0 | 2.8 |

[1]Weight Ratios.
[2]Conducted in 500 cc stainless steel "zipper" autoclave.
[3]Conducted in 300 cc autoclave equipped with glass liner.
[4]Molar Ratios.

EXAMPLE 14

The reaction of 50 g n-dodecane with 12 g paraformaldehyde as in Examples 9–13 using 10 g of di-tert-butyl peroxide (DTBP) as initiator was found to produce a concentration of tridecanols of about 3.5 percent. These alcohols were easily separated from unreacted hydrocarbon and other impurities by vacuum distillation through a small Vigreux column (108–125° C. at 0.6–0.7 mm Hg°). The positional isomers were not separated but proton and $^{13}C$ nuclear magnetic resonance spectroscopy indicated that most of the addition reactions took place in the 2-position of n-dodecane. Only a small amount of addition took place in the 1-position. The relative mole ratios of the positional isomers obtained are shown below.

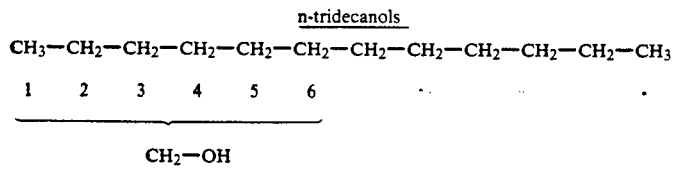

n-tridecanols

| Addition in Position | Relative Mole Ratio |
|---|---|
| 1- | small |
| 2- | 5.0 |
| 3- | 3.0 |
| 4- | 2.0 |
| 5- | 3.5 |
| 6- | 3.5 |

GLOSSARY

GC/FTIR: Gas Chromatography/Fourier Transform Infrared Spectroscopy
Di-tert-butyl peroxide
Area percent: Area of gas chromatography peak as a percent of the total area of all peaks.

What is claimed is:

1. A process for the manufacture of branched primary alcohols which comprises reacting a normal alkane with formaldehyde by contacting said alkane with paraformaldehyde or trioxane in a non-aqueous medium in the presence of a free radical initiator and recovering said branched primary alcohols as the product.

2. A process in accordance with claim 1 wherein said normal alkane has from about 3 to about 18 carbon atoms and the branched primary alcohol product has from 4 to 19 carbon atoms.

3. The process of claim 2 wherein said normal alkane has from about 10 to about 14 carbon atoms.

4. The process of claim 1 wherein the molar ratio of said alkane to said formaldehyde is in the range of from about 0.3 to about 5:1.

5. The process of claim 1 wherein the branched primary alcohol product is obtained as a mixture of positional isomers.

6. The process of claim 1 wherein the free radical initiator is an organic peroxide.

7. The process of claim 6 wherein said organic peroxide is selected from the group consisting of di-tert-butyl peroxide and tert-butyl peroxybenzoate.

8. The process of claim 1 wherein the free radical initiator is a hydroperoxide.

9. The process of claim 1 wherein said initiator is selected from azo compounds represented by the formula below.

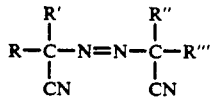

10. The process of claim 6 wherein the temperature is in the range from about 80° C. to 280° C.

11. The process of claim 8 wherein the temperature is in the range from about 80° C. to 280° C.

12. The process of claim 9 wherein the temperature is in the range from about 40° C. to 120° C.

13. The process of claim 1 wherein the formaldehyde is introduced as paraformaldehyde.

14. The process of claim 1 wherein the reaction mixture formed by the reactants is at least partially in the vapor state.

15. The process of claim 1 wherein the reaction mixture formed by the reactants is at least partially in the liquid state.

16. A method which comprises the steps of reacting normal alkanes with paraformaldehyde or trioxane in a non-aqueous medium at a temperature in the range of from about 80° C. to about 280° C. in the presence of about 0.02 to 25 percent by weight of a free radical initiator comprising at least one organic peroxide and recovering the branched primary alcohols from the reaction mixture.

17. The method of claim 16 wherein the normal alkane has from about 10 to about 14 carbon atoms.

18. The method of claim 16 wherein the molar ratio of said alkane to said formaldehyde is in the range of from about 0.3 to about 5:1.

19. A process for the manufacture of branched primary alcohols which comprises reacting a normal alkane characterized by the formula $CH_3\text{-}(CH_2)_x\text{-}CH_2\text{-}(CH_2)_y CH_3$ with formaldehyde by contacting said alkane with paraformaldehyde in a non-aqueous medium in the presence of a free radical initiator to produce a mixture of positional isomers of the branched primary alcohol characterized by the formula below.
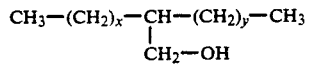
where x and y are integers ranging from 0 to about 15 and x + y can range from about 6 to about 14.
* * * * *